(12) United States Patent
Ooban et al.

(10) Patent No.: US 9,782,072 B2
(45) Date of Patent: Oct. 10, 2017

(54) OPHTHALMOLOGIC IMAGING APPARATUS AND OPHTHALMOLOGIC IMAGING METHOD

(71) Applicant: CANON KABUSHIKI KAISHA, Tokyo (JP)

(72) Inventors: Hideyuki Ooban, Saitama (JP); Yasuhiro Nakahara, Kawasaki (JP); Hiroshi Itoh, Machida (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/099,392

(22) Filed: Apr. 14, 2016

(65) Prior Publication Data

US 2016/0228002 A1 Aug. 11, 2016

Related U.S. Application Data

(63) Continuation of application No. 13/119,635, filed as application No. PCT/JP2010/003884 on Jun. 10, 2010, now Pat. No. 9,332,906.

(30) Foreign Application Priority Data

Jun. 11, 2009 (JP) .................................. 2009-140270
Jun. 7, 2010 (JP) .................................. 2010-130294

(51) Int. Cl.
  A61B 3/14 (2006.01)
  A61B 3/00 (2006.01)
  A61B 3/12 (2006.01)

(52) U.S. Cl.
  CPC . *A61B 3/14* (2013.01); *A61B 3/12* (2013.01)

(58) Field of Classification Search
  CPC .................................... A61B 3/14; A61B 3/12
  USPC .................................................. 351/206, 246
  See application file for complete search history.

*Primary Examiner* — Jack Dinh
(74) *Attorney, Agent, or Firm* — Canon USA, Inc. IP Division

(57) ABSTRACT

An ophthalmologic imaging apparatus that captures an image of a subject's eye is provided. The apparatus includes a focusing unit configured to focus light returned from the subject's eye that is illuminated by the light of a first wavelength, onto an imaging unit, and a moving unit configured to move the focusing unit based on an optical path length difference between the light of the first wavelength and the light of a second wavelength that is different from the first wavelength when light returned from the subject's eye that is illuminated by the light of the second wavelength is focused onto the imaging unit.

20 Claims, 11 Drawing Sheets

OPHTHALMOLOGIC IMAGING APPARATUS AND OPHTHALMOLOGIC IMAGING METHOD

This application is a Continuation of co-pending U.S. patent application Ser. No. 13/119,635 filed Mar. 17, 2011, which is a National Phase application of International Application PCT/JP 2010/003884, filed Jun. 10, 2010, which claims the benefit of Japanese Patent Application No. 2009-140270, filed Jun. 11, 2009 and Japanese Patent Application No. 2010-130294, filed Jun. 7, 2010. The disclosures of the above-named applications are hereby incorporated by reference herein in their entirety.

TECHNICAL FIELD

The present invention relates to ophthalmologic imaging apparatuses and ophthalmologic imaging methods for capturing an image of a subject's eye.

BACKGROUND ART

Fundus cameras that capture images of the fundus of a subject's eye include mydriatic fundus cameras and non-mydriatic fundus cameras. The mydriatic fundus cameras observe a subject's eye in which mydriatic drops are put using visible light and capture an image of the subject's eye. The non-mydriatic fundus cameras observe a subject's eye in which mydriatic drops are not put using near-infrared light and capture an image of the subject's eye. Further, there have been provided mydriatic and non-mydriatic fundus cameras that have functions of the mydriatic fundus cameras and the non-mydriatic fundus cameras. For example, Japanese Patent Application Laid-Open No. 9-66030 describes a mydriatic and non-mydriatic fundus camera that observes a subject's eye into which mydriatic drops are put using visible light by using an optical finder as means for observing a moving image. In this technology, when observing a subject's eye into which mydriatic drops are not put using near-infrared light, the optical path of reflected light from the fundus is changed to an optical path different from the path in the case of the observation of the subject's eye into which the mydriatic drops are put. The reflected light is guided to a charge-coupled device (CCD) that is image capturing means for a still image.

Further, Japanese Patent Application Laid-Open No. 8-256988 discusses a mydriatic and non-mydriatic fundus camera that is downsized using only one image capturing means. The technology of the No. 8-256988 discusses an optical element for optical path length correction that corrects an optical path difference generated due to a difference between the wavelengths of used light. The optical element is arranged in an optical path to a television camera that is an image capturing means.

Japanese Patent Application Laid-Open No. 10-43139 discusses a device that has image capturing means for capturing an image using reflected light from the fundus of an eye illuminated by visible light or infrared light. In the device, a bypass optical path for correcting an optical path length of the reflected light to the image capturing means is provided.

CITATION LIST

Patent Literature

[PTL 1]
Japanese Patent Application Laid-Open No. 9-66030

[PTL 2]
Japanese Patent Application Laid-Open No. 8-256988

[PTL 3]
Japanese Patent Application Laid-Open No. 10-43139

SUMMARY OF INVENTION

The present invention is based on an assumption that a common imaging unit is used to capture an image using light that has different wavelengths (observation light and photographing light). By the use of a focusing unit for focusing on the imaging unit, as compared to the technology discussed in Japanese Patent Application Laid-Open No. 9-66030, smaller, lighter, and simple-structured apparatuses having fewer components and novel structure can be provided.

According to an aspect of the present invention, an ophthalmologic imaging apparatus that captures an image of a subject's eye is provided. The apparatus includes a focusing unit configured to focus light returned from the subject's eye that is illuminated by the light of a first wavelength, onto an imaging unit, and a moving unit configured to move the focusing unit based on an optical path length difference between the light of the first wavelength and the light of a second wavelength that is different from the first wavelength when light returned from the subject's eye that is illuminated by the light of the second wavelength is focused onto the imaging unit.

According to another aspect of the present invention, an ophthalmologic imaging method for capturing an image of a subject's eye is provided. The method includes irradiating the subject's eye with the light of a first wavelength, focusing onto an imaging unit based on an optical path length difference between the light of the first wavelength and the light of a second wavelength that is different from the first wavelength, and irradiating the subject's eye with the light of the second wavelength.

According to another aspect of the present invention, an ophthalmologic imaging apparatus that captures an image of a subject's eye is provided. The apparatus includes an illumination optical system configured to irradiate the subject's eye with the light of a first wavelength and the light of a second wavelength that is different from the first wavelength, a photographing optical system having a focusing unit configured to focus light returned from the subject's eye that is illuminated by the illumination optical system onto an imaging unit, and a moving unit configured to move the focusing unit based on an optical path length difference between the light of the first wavelength and the light of the second wavelength.

According to the above-described ophthalmologic imaging apparatuses and ophthalmologic imaging method, the smaller, lighter, and simply structured apparatuses having fewer components and novel structure than before can be provided.

Further features and aspects of the present invention will become apparent from the following detailed description of exemplary embodiments with reference to the attached drawings.

BRIEF DESCRIPTION OF DRAWINGS

The accompanying drawings, which are incorporated in and constitute a part of the specification, illustrate exemplary embodiments, features, and aspects of the invention and, together with the description, serve to explain the principles of the invention.

DESCRIPTION OF EMBODIMENTS

Various exemplary embodiments, features, and aspects of the invention will be described in detail below with reference to the drawings.

Figure 1A:
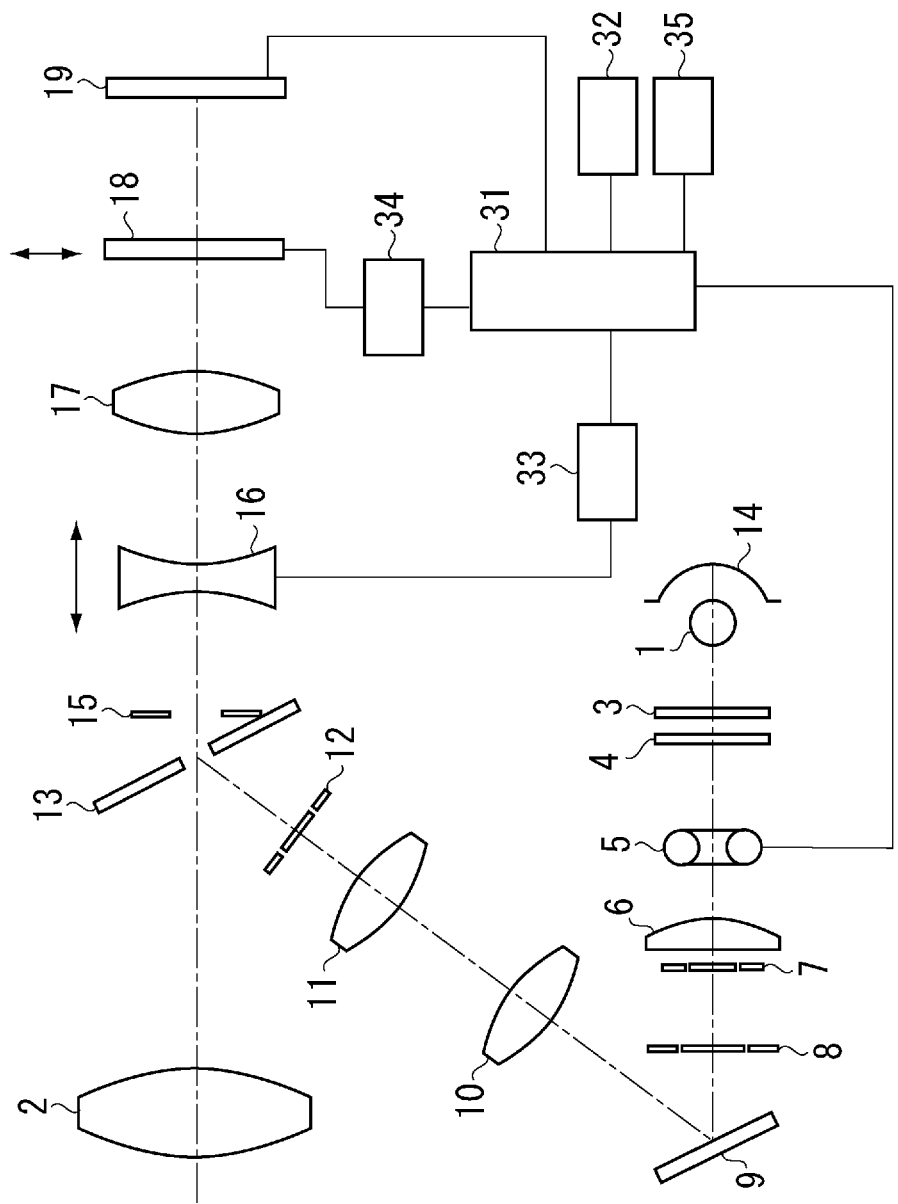
FIG. 1A is a view illustrating structure of fundus camera according to first and second exemplary embodiment of the present invention.

FIG. 1A is a view illustrating a structure of a non-mydriatic fundus camera according to an exemplary embodiment of the present invention. From an observation light source 1 that includes a halogen lamp to an objective lens 2 that faces a subject's eye is an illumination optical system. In the illumination optical system, the observation light source 1, a visible cut filter 3, a diffusion plate 4, a photographic light source 5 that comprises xenon tubes, a lens 6, a diaphragm 7, an eye-lens diaphragm 8, and a mirror 9 are arranged. In the reflecting direction of the mirror 9, relay lenses 10 and 11, a cornea stop 12, and a perforated mirror 13 are arranged in order. At the back of the observation light source 1, a reflecting mirror 14 is provided.

Figure 2A:
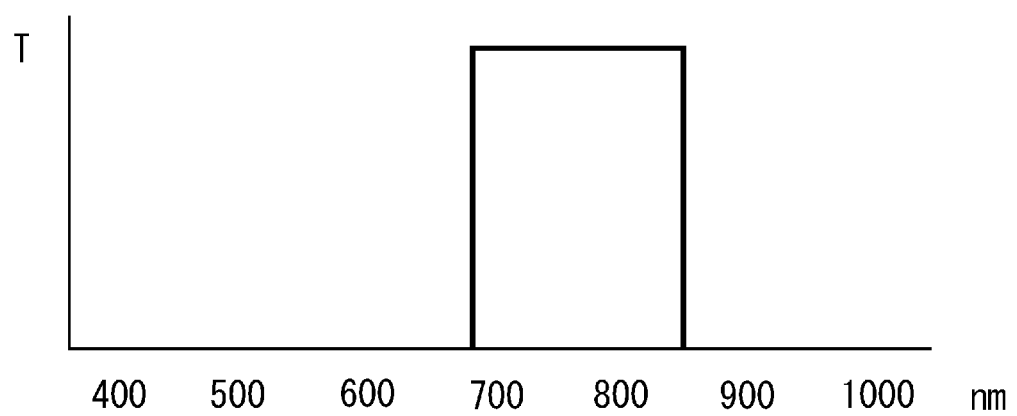
FIG. 2A illustrates characteristics of each wavelength band.

FIG. 2A illustrates transmission characteristics of the visible cut filter 3. The visible cut filter 3 does not pass light of visible wavelengths and passes light of near-infrared wavelengths of 680 nm or above.

At the back of the perforated mirror 13, an observation and photographing optical system is arranged. In the optical system, a photographic diaphragm 15, a focus lens 16 that can move along an optical path, an imaging lens 17, a near-infrared cut filter 18 that can be inserted into and removed from the optical path, and an image capturing unit 19 are arranged. The image capturing unit 19 has sensitivity ranging from visible light to near-infrared light that is invisible, and can output moving images and still images.

An output signal of the image capturing unit 19 is connected to a control unit (also referred to as display control unit) 31 and a monitor (also referred to as display unit) 32. An output signal of the control unit 31 is connected to the photographic light source 5, the focus lens 16 via a driving unit 33, and the near-infrared cut filter 18 (hereinafter, filters that select a wavelength of light for focusing on the image capturing unit may be referred to as wavelength selection units) via a driving unit 34. To the control unit 31, a photographing switch 35 for still image photographing is connected.

In moving image observation, light flux from the observation light source 1 passes through the visible cut filter 3 and is obtained as a near-infrared wavelength. The wavelength is used as illumination light (also referred to as light of a first wavelength). By the illumination light, a fundus of a subject's eye is illuminated. The image of the subject's eye is formed on an imaging surface of the image capturing unit 19 by the observation and photographing optical system. During the operation, the near-infrared cut filter 18 is retracted from the optical path by the driving unit 34. The operator performs positioning such that the fundus is positioned at a desired point while observing the moving image output from the image capturing unit 19 with the monitor 32. Then, in a state where the fundus and the image capturing unit 19 are conjugate to each other with respect to position, the control unit 31 controls the focus lens 16 through the driving unit 33 to perform focusing operation.

Figure 2B:
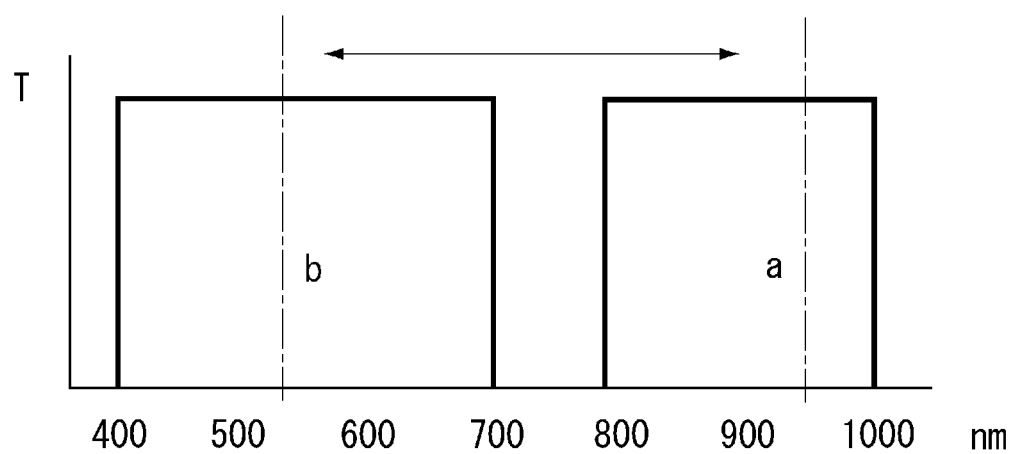
FIG. 2B illustrates characteristics of each wavelength band.

When capturing the image, as illumination light (also referred to as light of a second wavelength), visible light from the photographic light source 5 is used. When the photographing switch 35 is pressed, at a position where the focus lens 16 is being driven, the control unit 31 performs the focusing operation through the driving unit 33. At the same time, the photographic light source 5 emits light, and the control unit 31 inserts the near-infrared cut filter 18 into the observation and photographing optical system through the driving unit 34. Then, the image capturing unit 19 captures a still image, and the captured fundus image is displayed on the monitor 32. The control unit 31 stores an amount of movement of the focus lens 16 corresponding to an optical path difference between an arbitrary wavelength within a near-infrared wavelength range a of around 780 to 1000 nm and an arbitrary wavelength within a visible wavelength range b of around 400 to 700 nm shown in FIG. 2B. When the shooting is performed, the control unit 31 further moves the focus lens 16 by the stored amount from the in-focus position at the observation through the driving unit 33.

When the still image capturing ends, in order to return to the moving image observation, the control unit 31 moves back the focus lens 16 by the above-described amount via the driving unit 33 and retracts the near-infrared cut filter 18 from the optical path via the driving unit 34. The driving control of the focus lens 16 by the control unit 31 is not limited to the automatic focusing.

Figure 1B:
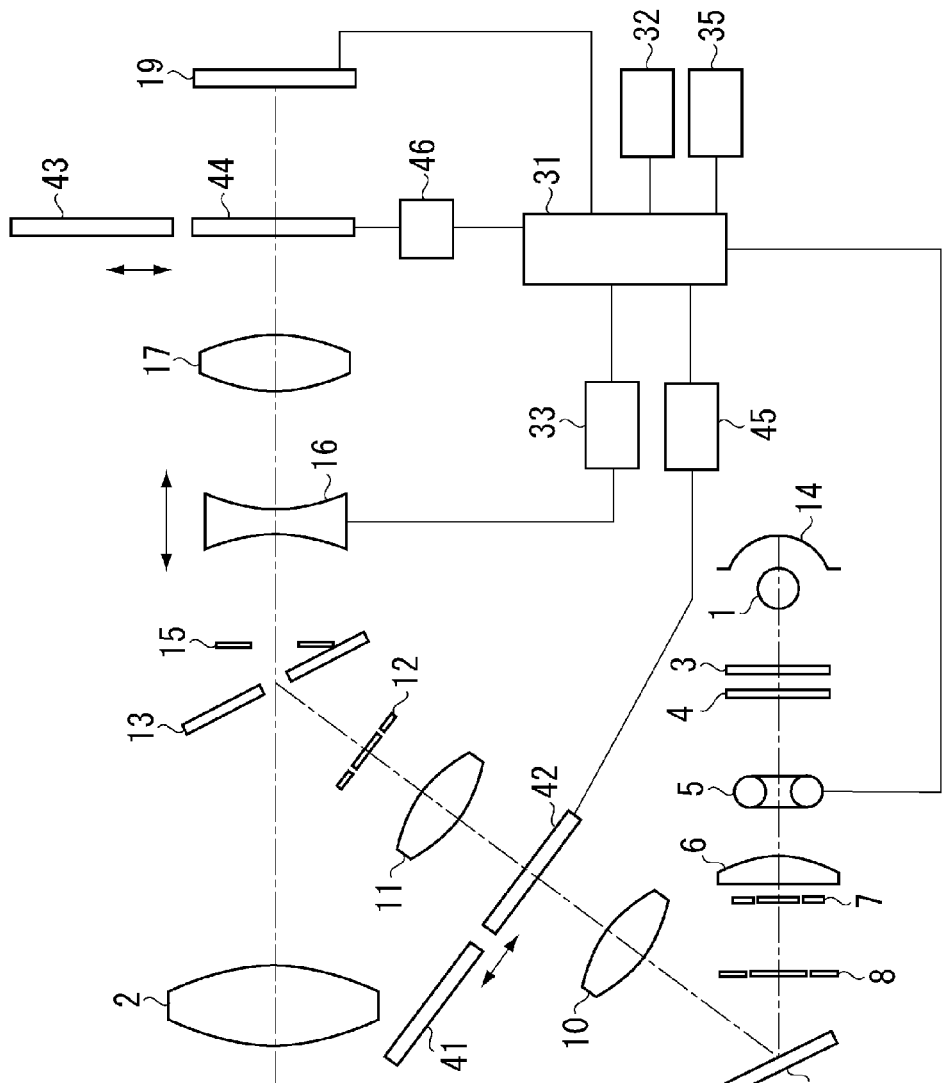
FIG. 1B is a view illustrating structure of fundus camera according to first and second exemplary embodiment of the present invention.

FIG. 1B illustrates a structure of a fundus camera that can perform autofluorescence photographing according to the second exemplary embodiment of the present invention. Reference numerals the same as those in the drawing used in the above-described description represent the same components. Between the relay lenses 10 and 11, an autofluorescence excitation filter 41 and an optical path length correction glass 42, which can be inserted into and removed from the optical path, are arranged so that they can be switched. Between the imaging lens 17 and the image capturing unit 19, an autofluorescence bandpass filter 43 and an optical path length correction glass 44 are arranged so that they can be switched. Output of the control unit 31 is connected to the autofluorescence excitation filter 41 and the optical path length correction glass 42 through a driving unit 45, and also connected to the autofluorescence bandpass filter 43 and the optical path length correction glass 44 through the driving unit 46.

Figure 3A:
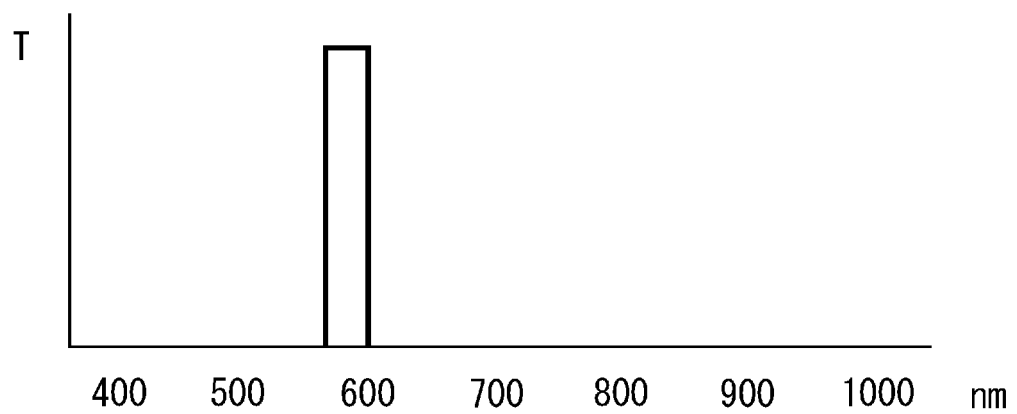
FIG. 3A illustrates transmission characteristics of each filter.
Figure 3B:
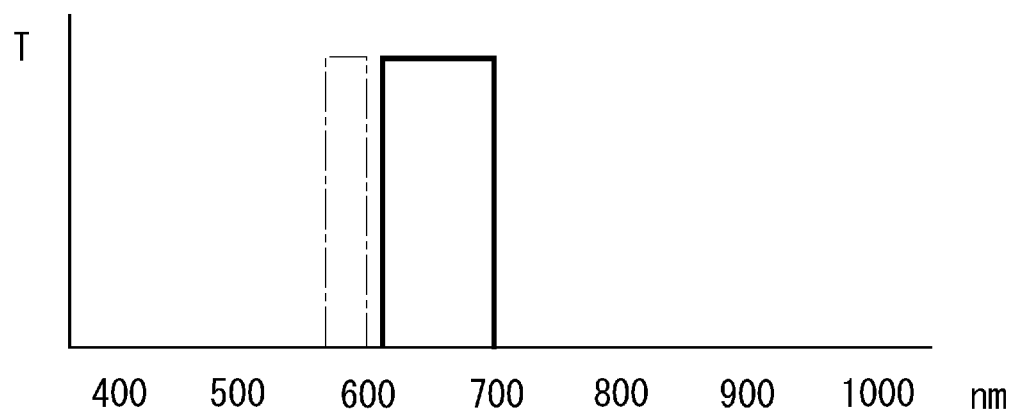
FIG. 3B illustrates transmission characteristics of each filter.

FIG. 3A illustrates transmission characteristics of the autofluorescence excitation filter 41. The autofluorescence excitation filter 41 transmits wavelengths of around 580 nm and blocks the other wavelengths. FIG. 3B illustrates transmission characteristics of the autofluorescence bandpass filter 43. The autofluorescence bandpass filter 43 transmits wavelengths of around 620 to 700 nm and blocks the other wavelengths. In FIG. 3B, the dotted line shows the transmission characteristics of the autofluorescence excitation filter 41 in FIG. 3A. It shows that the transmission band in FIG. 3B does not overlap with the transmission band of the autofluorescence bandpass filter 43.

To observe an moving image, as illumination light, near-infrared light is used similarly to the above-described exemplary embodiment. In the illumination optical system, the control unit 31 inserts the optical path length correction glass 42 into the optical path through the driving unit 45. In the observation and photographing optical system, the control unit 31 inserts the optical path length correction glass 44 into the optical path through the driving unit 46.

The operator performs positioning such that the image of the fundus is positioned at a desired point while observing the moving image output from the image capturing unit 19 with the monitor 32. Then, the control unit 31 controls the focus lens 16 through the driving unit 33 to perform focusing operation.

To photograph a still image, as illumination light, visible light from the photographic light source 5 is used. When the photographing switch 35 is pressed, in synchronization with the shooting, in the illumination optical system, the control unit 31 switches the optical path length correction glass 42 to the autofluorescence excitation filter 41 via the driving unit 46. In the observation and photographing optical system, the control unit 31 switches the optical path length correction glass 44 to the autofluorescence bandpass filter 43 via the driving unit 46 in synchronization with the shooting, the control unit 31 performs focusing control of the focus lens 16. Simultaneously, the photographic light source 5 emits light and still image photographing is performed. The image captured as an autofluorescence image generated at the fundus is displayed on the monitor 32.

Figure 2C:
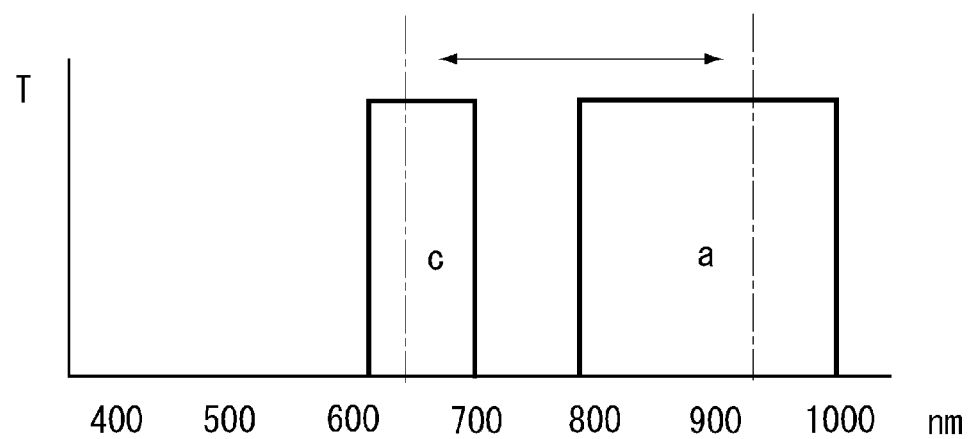
FIG. 2C illustrates characteristics of each wavelength band.

An optical path difference is generated due to a difference between a wavelength within the near-infrared wavelength range a of about 780 to 1000 nm and a wavelength within an autofluorescence fluorescence wavelength range c of about 620 to 700 nm shown in FIG. 2C. The control unit 31 stores a movement amount of the focus lens 16 corresponding to the optical path difference. In synchronization with the shooting, the control unit 31 moves the focus lens 16 by the movement amount.

When the still image photographing ends, in order to return to the moving image observation, in the illumination optical system, the control unit 31 switches the autofluorescence excitation filter 41 to the optical path length correction glass 42. In the observation and photographing optical system, the control unit 31 retracts the autofluorescence bandpass filter 43 and moves back the focus lens 16 by the movement amount.

When the shooting is performed using visible light, the near-infrared filter can be provided at a desired position in the illumination optical system or the observation and photographing optical system, and the thickness of the optical filter is not limited to a certain thickness.

In a fundus camera according to the third exemplary embodiment of the present invention, the visible cut filter 3 in front of the observation light source 1 is removed from FIG. 1B. By the configuration, illumination light from the observation light source 1 selectively includes visible light.

To observe a moving image, as illumination light (also referred to as light of a first wavelength), visible light is used. In the illumination optical system, the control unit 31 performs control to insert the optical path length correction glass 42 into the optical path via the driving unit 45. In the observation and photographing optical system, the control unit 31 performs control to insert the optical path length correction glass 44 into the optical path via the driving unit 46.

The operator performs positioning such that the image of the fundus is positioned at a desired point while observing the moving image output from the image capturing unit 19 with the monitor 32. Then, the control unit 31 drives the focus lens 16 to perform focusing operation.

To photograph a still image, as illumination light (also referred to as light of a second wavelength), visible light is used. When the photographing switch 35 is pressed, in the illumination optical system, the control unit 31 switches the optical path length correction glass 42 to the autofluorescence excitation filter 41 via the driving unit 45. In the observation and photographing optical system, the control unit 31 switches the optical path length correction glass 44 to the autofluorescence bandpass filter 43 via the driving unit 46. Further, in synchronization with the shooting, the control unit 31 performs control to move the focus lens 16. Simultaneously, the photographic light source 5 emits light and the still image photographing is performed. The captured image is displayed on the monitor 32.

Figure 2D:
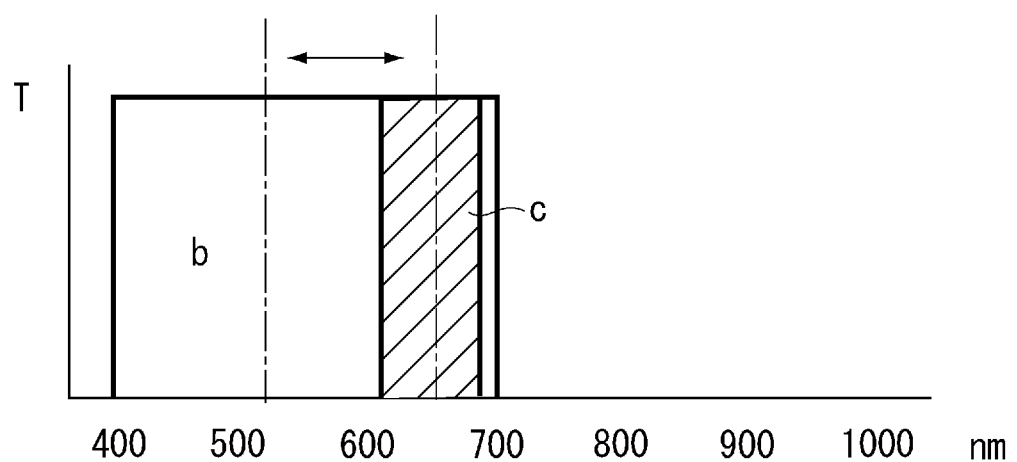
FIG. 2D illustrates characteristics of each wavelength band.

The control unit 31 stores a movement amount corresponding to an optical path difference generated due to a difference between a wavelength within the visible wavelength range b of around 400 to 700 nm and a wavelength within the autofluorescence fluorescence wavelength range c of around 620 to 700 nm shown in FIG. 2D. In synchronization with the shooting, the control unit 31 moves the focus lens 16 by the stored movement amount.

When the still image photographing ends, in order to return to the moving image observation, the control unit 31 switches the autofluorescence excitation filter 41 to the optical path length correction glass 42. Further, the control unit 31 switches the autofluorescence bandpass filter 43 to the optical path length correction glass 44 and moves back the focus lens 16 by the stored movement amount.

A fundus camera according to the fourth exemplary embodiment of the present invention includes an infrared fluorescent (ICG (Indocyanine green)) excitation filter 51 and an infrared fluorescent (ICG) bandpass filter 53 in replace of the autofluorescence excitation filter 41 and the autofluorescence bandpass filter 43 illustrated in FIG. 1B respectively.

Between the imaging lens 17 and the image capturing unit 19, the infrared fluorescent (ICG) bandpass filter 53 and the optical path length correction glass 44 are arranged so that they can be switched. The infrared fluorescent excitation filter 51 and the optical path length correction glass 42 are driven in response to an instruction by the control unit 31 by the driving unit 45. The infrared fluorescent bandpass filter 53 and the optical path length correction glass 44 are driven by the driving unit 46.

Figure 3C:
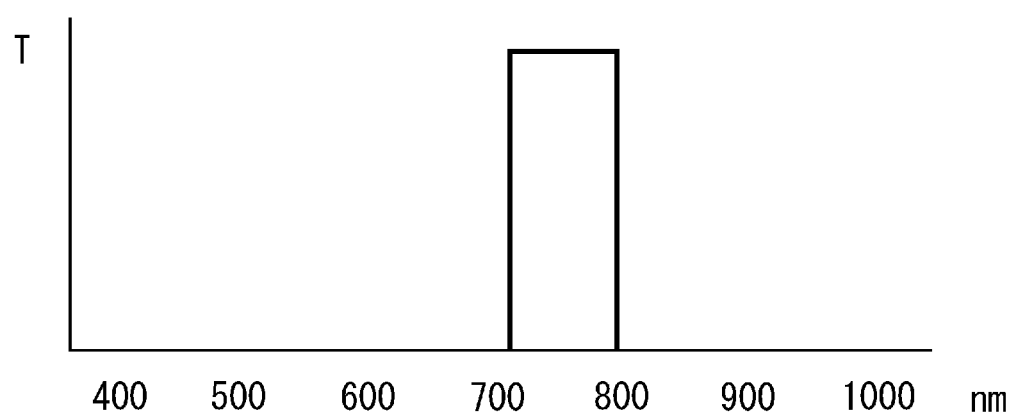
FIG. 3C illustrates transmission characteristics of each filter.
Figure 3D:
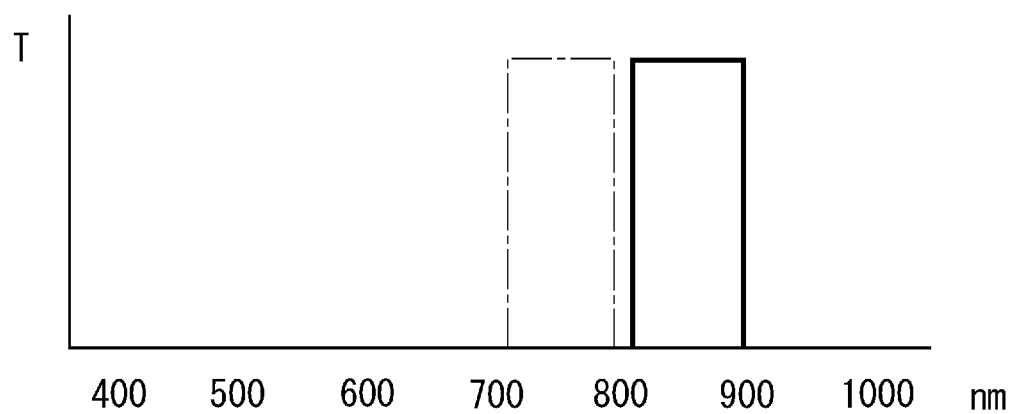
FIG. 3D illustrates transmission characteristics of each filter.

FIG. 3C illustrates transmission characteristics of the infrared fluorescent excitation filter 51. The infrared fluorescent excitation filter 51 transmits wavelengths of around 720 to 800 nm and blocks the other wavelengths. FIG. 3D illustrates transmission characteristics of the infrared fluorescent bandpass filter 53. The infrared fluorescent (ICG) bandpass filter 53 transmits wavelengths of around 820 to 900 nm and blocks the other wavelengths. The dotted line shows the transmission characteristics of the infrared fluorescent excitation filter 51 in FIG. 3D. It shows that the transmission band in FIG. 3D does not overlap with the transmission band of the infrared fluorescent bandpass filter 53.

To observe a moving image, near-infrared wavelength is used as illumination light. In the illumination optical system, the control unit 31 inserts the optical path length correction glass 42 into the optical path via the driving unit 45. In the observation and photographing optical system, the control unit 31 inserts the optical path length correction glass 44 via the driving unit 46.

The operator performs positioning such that the image of the fundus is positioned at a desired point while observing the moving image output from the image capturing unit 19 with the monitor 32. Then, the control unit 31 drives the focus lens 16 to perform focusing operation.

To observe a still image, visible wavelength is used as illumination light. When the photographing switch 35 is pressed, in the illumination optical system, the control unit 31 switches the optical path length correction glass 42 to the infrared fluorescent excitation filter 51 via the driving unit 45. In the observation and photographing optical system, the control unit 31 switches the optical path length correction glass 44 to the infrared fluorescent bandpass filter 53 via the driving unit 46. Further, in synchronization with the shooting, the control unit 31 performs focusing control of the focus lens 16. Simultaneously, the photographic light source 5 emits light and the still image photographing is performed. The captured image is displayed on the monitor 32.

Figure 2E:
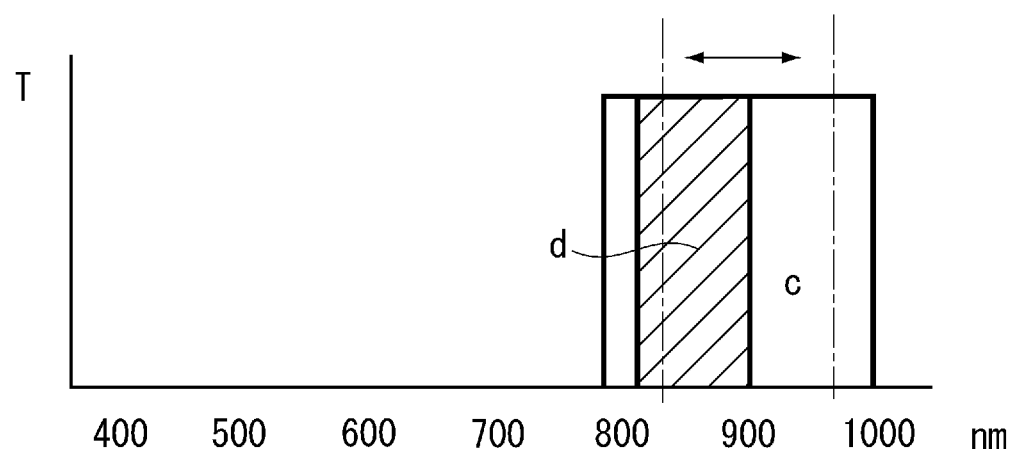
FIG. 2E illustrates characteristics of each wavelength band.

The control unit 31 stores a movement amount corresponding to an optical path difference generated due to a difference between a wavelength within the near-infrared wavelength range a of around 780 to 1000 nm and a wavelength within an infrared fluorescence fluorescence wavelength range d of around 820 to 900 nm shown in FIG. 2E. In synchronization with the shooting, the control unit 31 moves the focus lens 16 by the movement amount.

When the still image photographing ends, in order to return to the moving image observation, the control unit 31 switches the infrared fluorescent excitation filter 51 to the optical path length correction glass 42. Further, the control unit 31 switches the infrared fluorescent bandpass filter 53 to the optical path length correction glass 44. Further, the control unit 31 moves back the focus lens 16 to the original position by the movement amount.

In the above-described exemplary embodiments of the present invention, a dichroic mirror that can be inserted into and removed from the observation and photographing optical path can be used to correct the optical path when a light flux splitting unit for optical path splitting is inserted or retracted.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Applications No. 2009-140270 filed Jun. 11, 2009 and No. 2010-130294 filed Jun. 7, 2010, which are hereby incorporated by reference herein in their entirety.

The invention claimed is:

1. An ophthalmologic imaging apparatus that captures an image of a fundus of a subject's eye, the apparatus comprising:
    observation imaging optical system including a focusing lens movable in an optical axis direction and an imaging element having sensitivity in a visible area and an infrared area, the observation imaging optical system being configured to obtain, using the imaging element, both a fundus observation image with light of a first wavelength and a fundus photograph image with light of a second wavelength different from the first wavelength;
    a wavelength selection unit capable of being inserted into or retracted from an optical path of the observation imaging optical system; and
    a control unit configured to move the focusing lens to an in-focus position for obtaining the fundus photograph image with the light of the second wavelength, on the basis of (a) a difference between the first wavelength and the second wavelength and (b) the wavelength selection unit being inserted into or retracted from the optical path.

2. The ophthalmologic imaging apparatus according to claim 1, wherein light of the first wavelength is infrared light, and light of the second wavelength is invisible light.

3. The ophthalmologic imaging apparatus according to claim 1, wherein the fundus photograph image obtained with the light of the second wavelength is a fundus photograph image with visible fluorescence.

4. The ophthalmologic imaging apparatus according to claim 1, wherein the control unit is configured to move the focusing lens to the in-focus position for obtaining the fundus photograph image with the light of the second wavelength after the control unit has input a trigger signal for capturing the fundus photograph image with the light of the second wavelength.

5. The ophthalmologic imaging apparatus according to claim 4, further comprising an imaging unit configured to capture the fundus photograph image with the light of the second wavelength after the focusing lens has been moved to the in-focus position for obtaining the fundus photograph image with the light of the second wavelength by the control unit.

6. The ophthalmologic imaging apparatus according to claim 1,
    wherein the wavelength selection unit selects a wavelength of light to be focused on the imaging element, and
    wherein the control unit controls the wavelength selection unit in such a manner that the wavelength selection unit is inserted into or retracted from the optical path.

7. The ophthalmologic imaging apparatus according to claim 1, wherein the wavelength selection unit is any one of a dichroic minor capable of being inserted into and removed from the optical path of the observation imaging optical system, an autofluorescence filtration member, an infrared fluorescent filtration member, and a near-infrared light cut filter.

8. The ophthalmologic imaging apparatus according to claim 1, wherein the control unit moves the focusing lens to the in-focus position for obtaining the fundus photograph image with the light of the second wavelength by moving the focusing lens by a movement amount corresponding to (a) the difference and (b) the insert or the retraction.

9. The ophthalmologic imaging apparatus according to claim 8, wherein the movement amount differs between a case of performing autofluorescence photographing for the fundus and a case of performing a photographing other than the autofluorescence photographing for the fundus.

10. An ophthalmologic imaging apparatus that captures an image of a fundus of a subject's eye, the apparatus comprising:
    an observation imaging optical system including a focusing lens movable in an optical axis direction and an imaging element having sensitivity in a visible area and an infrared area, the observation imaging optical system being configured to obtain, using the imaging element, both a fundus observation image with light of a first wavelength and a fundus photograph image with light of a second wavelength different from the first wavelength;
    a wavelength selection unit capable of being inserted into or retracted from an optical path of the observation imaging optical system; and
    a control unit configured to move the focusing lens on the basis of the wavelength selection unit being inserted into or retracted from the optical path.

11. The ophthalmologic imaging apparatus according to claim 10,
    wherein the wavelength selection unit selects a wavelength of light to be focused on the imaging element, and
    wherein the control unit controls the wavelength selection unit in such a manner that the wavelength selection unit is inserted into or retracted from the optical path.

12. The ophthalmologic imaging apparatus according to claim 10, wherein the wavelength selection unit is any one of a dichroic minor capable of being inserted into and removed from the optical path of the observation imaging optical system, an autofluorescence filtration member, an infrared fluorescent filtration member, and a near-infrared light cut filter.

13. The ophthalmologic imaging apparatus according to claim 10, wherein the control unit moves the focusing lens so that an optical path length difference caused by the insert or retraction is corrected.

14. An ophthalmologic imaging apparatus that captures an image of a fundus of a subject's eye, the apparatus comprising:
    an observation imaging optical system including a focusing lens movable in an optical axis direction and an imaging element having sensitivity in a visible area and an infrared area, the observation imaging optical system being configured to obtain, using the imaging element, both a fundus observation image with light of a first wavelength and a fundus photograph image with light of a second wavelength different from the first wavelength; and
    a control unit configured to move the focusing lens to an in-focus position for obtaining the fundus observation image with the light of the first wavelength, and, after the focusing lens has been moved to the in-focus position for obtaining the fundus observation image with the light of the first wavelength, move the focusing lens to an in-focus position for obtaining the fundus photograph image with the light of the second wavelength, in consideration of an optical path difference between a case where fundus observation with the light of the first wavelength is performed and a case where fundus photographing with the light of the second wavelength is performed.

15. A control method of an ophthalmologic imaging apparatus including an observation imaging optical system including a focusing lens movable in an optical axis direction and an imaging element having sensitivity in a visible area and an infrared area, the observation imaging optical system being configured to obtain, using the imaging element, both a fundus observation image with light of a first wavelength and a fundus photograph image with light of a second wavelength different from the first wavelength; and a wavelength selection unit capable of being inserted into or retracted from an optical path of the observation imaging optical system; the control method comprising a step of moving the focusing lens to an in-focus position for obtaining the fundus photograph image with the light of the second wavelength, on the basis of (a) a difference between the first wavelength and the second wavelength and (b) the wavelength selection unit being inserted into or retracted from the optical path.

16. A non-transitory computer-readable storage medium storing a program for causing a computer to execute steps in the control method according to claim 15.

17. A control method of an ophthalmologic imaging apparatus including an observation imaging optical system including a focusing lens movable in an optical axis direction and an imaging element having sensitivity in a visible area and an infrared area, the observation imaging optical system being configured to obtain, using the imaging element, both a fundus observation image with light of a first wavelength and a fundus photograph image with light of a second wavelength different from the first wavelength and a wavelength selection unit capable of being inserted into or retracted from an optical path of the observation imaging optical system; the control method comprising a step of moving the focusing lens on the basis of the wavelength selection unit being inserted into or retracted from the optical path.

18. A non-transitory computer-readable storage medium storing a program for causing a computer to execute steps in the control method according to claim 17.

19. A control method of an ophthalmologic imaging apparatus including an observation imaging optical system including a focusing lens movable in an optical axis direction and an imaging element having sensitivity in a visible area and an infrared area, the observation imaging optical system being configured to obtain, using the imaging element, both a fundus observation image with light of a first wavelength and a fundus photograph image with light of a second wavelength different from the first wavelength; the control method comprising a step of moving the focusing lens to an in-focus position for obtaining the fundus observation image with the light of the first wavelength, and, after the focusing lens has been moved to the in-focus position for obtaining the fundus observation image with the light of the first wavelength, move the focusing lens to an in-focus position for obtaining the fundus photograph image with the light of the second wavelength, in consideration of an optical path difference between a case where fundus observation with the light of the first wavelength is performed and a case where fundus photographing with the light of the second wavelength is performed.

20. A non-transitory computer-readable storage medium storing a program for causing a computer to execute steps in the control method according to claim 19.

\* \* \* \* \*